United States Patent [19]

Pietkivitch

[11] Patent Number: 4,676,748
[45] Date of Patent: Jun. 30, 1987

[54] OCCLUSAL IMPRESSION DEVICE
[75] Inventor: Albert Pietkivitch, Racine, Wis.
[73] Assignee: Walter A. Hackler, Irvine, Calif.
[21] Appl. No.: 882,948
[22] Filed: Jul. 7, 1986
[51] Int. Cl.[4] .............................................. H61C 9/00
[52] U.S. Cl. ...................................................... 433/71
[58] Field of Search .................................... 433/71, 38

[56] References Cited
U.S. PATENT DOCUMENTS

| 1,303,545 | 5/1919 | Downie | 433/71 |
|---|---|---|---|
| 2,183,624 | 12/1939 | Schwartz | 433/71 |
| 3,064,354 | 11/1962 | Pos | 433/71 |
| 3,250,004 | 5/1966 | Jones | 433/38 |
| 4,472,140 | 9/1984 | Lustig | 433/71 |

Primary Examiner—Robert Peshock
Attorney, Agent, or Firm—Walter A. Hackler

[57] ABSTRACT

An occlusal impression device includes first and second impression waxes for deforming in response to pressed engagement therewith and a continuous sheet support means laminated thereto for supporting the impression waxes and for placing the impression waxes into a mouth in a position for engagement with mandibular and maxillary teeth. The impression waxes and support means are flat, coplanar and include a grip portion which extends from the support means to enable insertion of the first and second impression waxes into a mouth in a position for simultaneous engagement with all of the mandible and maxilla teeth. The support means is configured for folding from a storage position to an exposed position and includes a surface thereon for permanently recording the identification of the patient making the impressions in the occlusal impression device.

22 Claims, 6 Drawing Figures

U.S. Patent   Jun. 30, 1987   Sheet 2 of 2   4,676,748
FIG. 4.
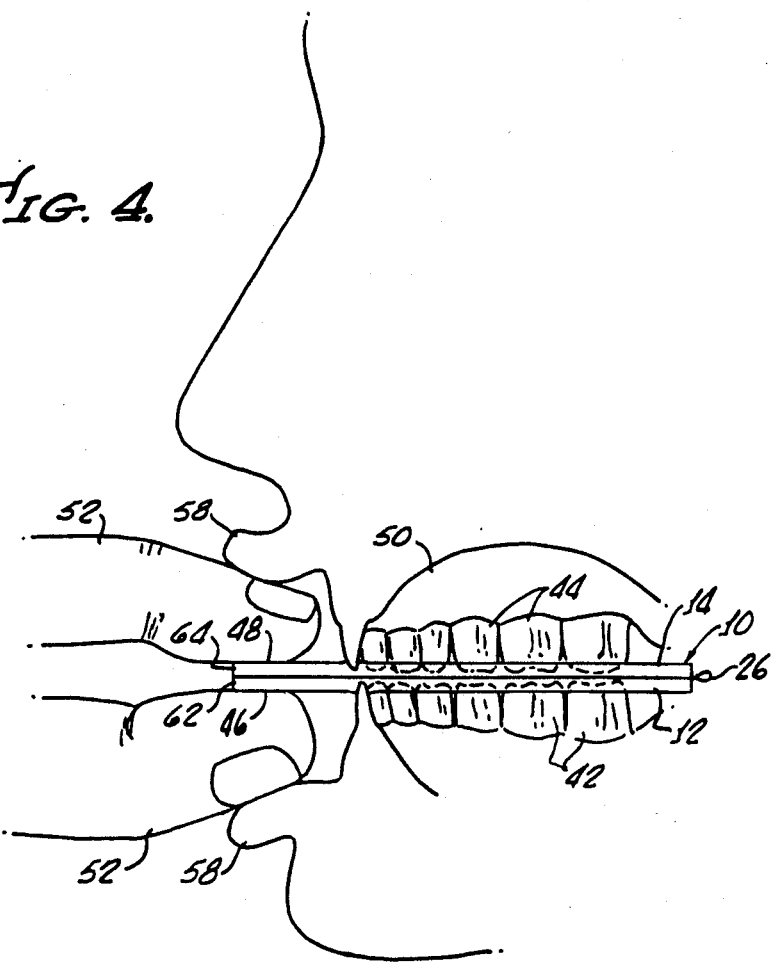
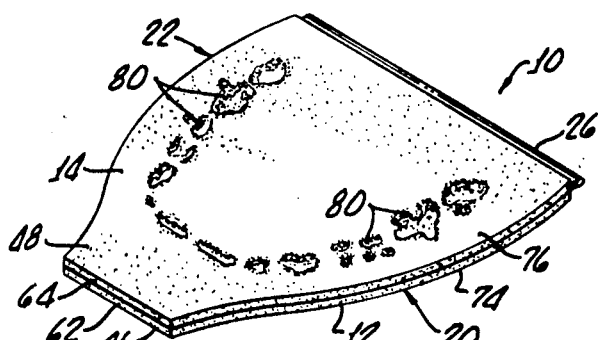
FIG. 5.
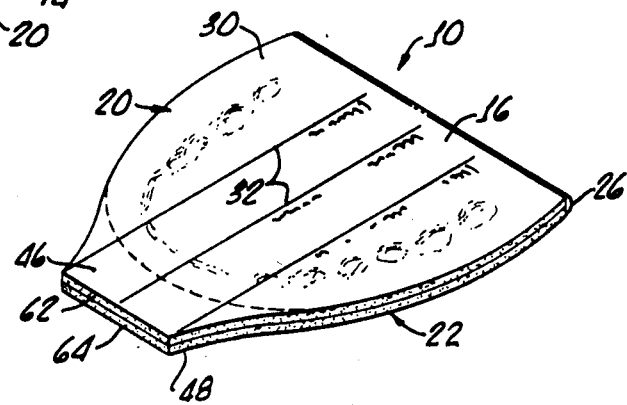
FIG. 6.

OCCLUSAL IMPRESSION DEVICE

The present invention generally relates to orthodontics and is more particularly related to an occlusal impression device for determining the bite of mandible and maxilla teeth.

Orthodontia has long been an important branch of dentistry for correcting irregularities in teeth, for both cosmetic and functional reasons. As is well known, correct spacing and proper alignment of mandible and maxilla teeth may be necessary for proper mastication of foods.

Irregularities in teeth, such as spacing or twisting thereof, are many times corrected through the use of rubber-like positioners, or other type of orthodontic devices, which, when worn over a length of time, urge the teeth into a preselected, or desired, position.

Since each person's mouth is different, it is easily appreciated that such positions must be custom-made for each individual set of teeth. This is accomplished by making a casting of a person's mandible and maxillary teeth to determine their existing irregularities. These castings are typically used by a laboratory technician in the creation of orthodontic devices, for example, a set of positioners to be worn for correcting the irregularities of the teeth.

While some dental practitioners may have on-site facilities for the manufacture of orthodontic devices, most of this work is done by independent laboratories situated throughout the country to which the castings are sent. In order to recreate the actual alignment of the mandible and the maxilla teeth as they existed in the mouth when the castings were made, an occlusal impression of the mandible and maxilla teeth is made in order to record the precise alignment therebetween or study the alignment of the castings.

This occlusion impression is typically done in wax, soft metal or plastic, which is fitted between the mandible and maxilla teeth by the dentist's fingers, or forceps. The patient causes an impression by biting into the wax. This occlusion impression is also sent to the laboratory technician so that the precise alignment of the mandible and maxilla teeth can be recreated in the laboratory. After this alignment is made, the mandible and maxilla teeth are appropriately marked and the individual cast teeth cut from the casting and realigned to a desired position and the positioners, or other orthodontic devices, made therefrom. Subsequent wearing of the positioners by the patient causes the patient's teeth to move into the preselected or desired position.

This procedure has been used for many years, and throughout that time there has always been difficulty in providing to remote dental laboratories a clear identifiable record of the occlusion impression. One of the problems associated with the procedure is that the materials used for the occlusal impression are of wax, or wax-like substances, which are difficult to write on. In this case, the identification of the patient with the occlusal impression is typically done on a separate piece of paper, which is easily separated and, therefore, lost from the occlusal impression, either by the dentist supplying the impression or the laboratory receiving the impression. It must be borne in mind that hundreds, if not thousands, of such impressions are typically being processed at one time and, hence, such loss or misidentification of impressions may occur on a regular basis.

In addition, the wax-like substances used for impressions are often difficult to handle and position in the mouth, with such positioning requiring typically uncomfortable entry of a dentist's fingers, or forceps, in a patient's mouth. In this procedure, a dentist must be able to properly position the material and withdraw his fingers, or forceps, while hoping that the patient does not disturb the position of the impression material before he bites thereinto.

Yet an additional problem associated with present impression materials is the fact that such wax, or wax-like materials, are fragile, particularly when subjected to cold temperatures. Cold or freezing temperatures are not expected within a dentist's office of dental laboratory, however, the shipment of the impression from one facility to another exposes it to outside weather which, in the winter, causes the wax material to be quite fragile. In many instances, rough handling by delivery services coupled with cold water results in the impression being received by the laboratory in a fractured condition which usually renders it either difficult or impossible to use. Needless to say, when the impressions are received in broken pieces, they are even more susceptible to comingling with other impressions, thereafter rendering the identity of the patient from which the impressions became impossible to determine and, hence, impossible to determine the proper alignment of the patient's mandible and maxilla teeth.

Still another problem associated with present occlusal impressions is the fact that they are unprotected after the impression is made. Since the materials are relatively soft, wax or wax-like materials, subsequent rough handling of the impression may damage it or cause additional impressions on the existing impression to make it useless in determining the alignment of the patient's teeth.

The present invention is directed to an occlusal impression device that is easy to use, offers protection for the impression, resists separation of the impression, due to physical damage and cold temperatures, and offers a way to permanently record the history of the impression. The present invention, in fact, solves all of the problems heretofore experienced with occlusal impression devices. First, it enables proper placement of the impression material within the mouth of a patient without the entry of a dentist's fingers, or forceps. In addition, it ensures that the impressions so made do not break apart due to rough physical handling, or cold temperatures, and ensures proper alignment of both mandible teeth and maxilla teeth with one another. Also incorporated into the invention is a recording system for permanently identifying the impressions made with the patient making the impressions.

SUMMARY OF THE INVENTION

In accordance with the present invention, an occlusal impression device includes impression means for deforming in response to pressed engagement therewith and support means fixed to the impression means for both supporting the impression means and for placing the impression means into a mouth in a position for engagement with at least one tooth therein. The support means includes grip means for enabling placement of the impression means within the mouth without entry of the grip means into the mouth. Hence, the present invention offers the advantage of enabling a dentist to use the grip means to place the impression means into the mouth of a patient without any entry of the dentist's fingers, or forceps, into the patient's mouth and to hold the impression means in the mouth while the patient causes deformation, or impression, in the impression means.

More particularly, the impression means and the support means are flat, coplanar and each generally has a mandibular or maxilliary arch shape. The impression means may be sized for engagement with all of the mandible or maxilla teeth, and the grip means may comprise an extension of the support means and project outwardly from a central portion of the mandibular or maxilliary arch, with a length sufficient to extend beyond the labia when the impression means is inserted into a mouth in position for engagement of all the mandible or maxilla teeth.

In order to simultaneously take the impression of both the mandible teeth and the maxilla teeth, the present invention may provide for first and second impression means for deforming in response to pressed engagement therewith.

First support means fixed to the first impression means support the first impression means and enable placing the first impression means in a mouth in position for engagement with at least one mandible tooth therein, and second support means, fixed to the second impression means, support the second impression means and enable placing the second impression means into the mouth in the position for engagement with at least one maxilla tooth therein.

Importantly, the first and the second support means are hingeably attached to one another to enable movement of the first and second impression means from a storage position in which the first and second impression means face one another, with the first and second support means protecting the first and second impression means from impression, to an exposed position in which the first and second impression means face outwardly from one another, ready for simultaneous impression by occlusion of mandible and maxilla teeth. In this configuration, the first impression means is sized for engagement with all of the mandible teeth and the second impression means is sized for engagement with all of the maxilla teeth.

It is preferable that the first and second impression means have identical outside perimeters in order to provide a means for aligning the front and second impression means with one another prior to impression thereof.

Hence, it is to be realized that the support means not only are available for holding the impression means in proper position within the mouth, but also provide a means of protecting the impression means from subsequent impression when it is in a stored position.

Preferably, the first and second support means are formed from a single sheet of flexible material and the center portion of the flexible material functions as a hinge. It is also preferable that the first and second impresssion means and the first and second support means are mirror images of one another, respectively, and the hinge means is configured for enabling the first and second support means to abut one another, when the first and second impression means are in the exposed position. As hereinbefore noted, this exposed position readies the appliance for recording the occlusal impression in the impression means which may comprise a wax material.

Importantly, at least one of the first or second support means has a surface thereon capable of receiving written indicia for recording the use of the occlusal appliance. This surface is disposed on an opposite side of the first or second support means rather than a side on which the first or second impression means is disposed. Hence, the surface capable of receiving written indicia is visible when the first and second impression means are in a closed position.

Since the support means and the impression means are fixed to one another, a permanent record of the origin of the impression is maintained in an inseparable relationship with the impression means.

The support means is laminated to the impression means in order that the support means can prevent separation of pieces of the support means from one another if the impression means should fracture. Thus, a feature of the present invention prevents fracture of the impression means, as a result of shock and cold temperatures during transit of the occlusal impression from the dentist's office to the laboratory, from causing separation of the impression means into separate pieces. Since fractured pieces of the impression means are held in alignment with one another and to the support means, a complete record of the occlusal impression is preserved.

BRIEF DESCRIPTION OF THE DRAWINGS

The advantages and features of the present invention will appear from the following description when considered in conjunction with the accompanying drawings, in which:

FIG. 4 is a side view of the occlusal impression device inserted into the mouth of a patient, particularly exhibiting the feature of the present invention in which a grip is provided, such that the fingers of a dentist are not inserted into the mouth, thus facilitating an occlusal impression without interference with the dentist's fingers;

FIG. 5 is a perspective view of the occlusal impression device after recording the occlusal impression of a patient; and, FIG. 6 is a perspective view of the occlusal impression device showing it in a stored configuration, protecting and preserving the recorded occlusal impression of the patient.

DETAILED DESCRIPTION

Figure 1:
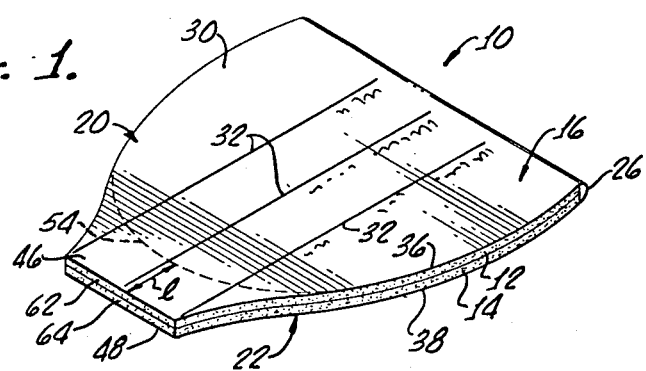
FIG. 1 is a perspective view of an occlusal impression device in accordance with the present invention in a closed position, showing a continuous sheet which provides means for supporting impression waxes thereon with the impression waxes facing one another and the support sheet turned outwardly to protect the impression waxes from impression.
Figure 2:
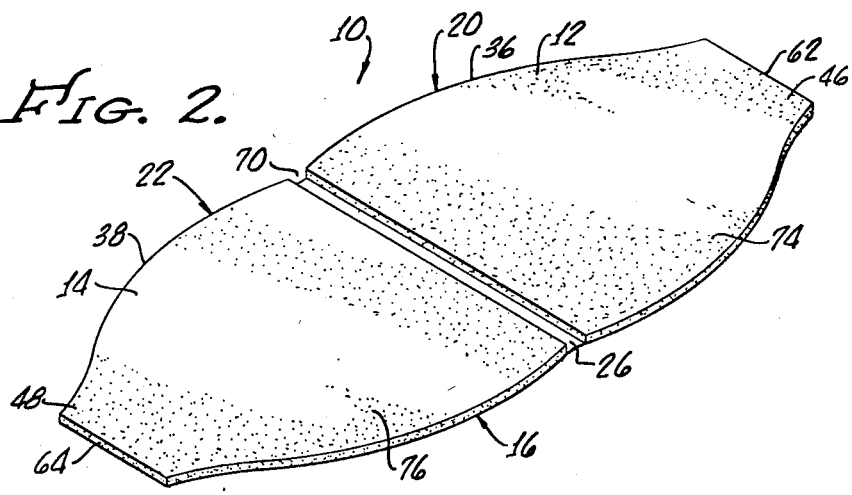
FIG. 2 is a perspective view of the occlusal impression device in accordance with the present invention unfolded to a planar position more clearly showing a separation between the wax impression media for enabling folding of the occlusal impression device.
Figure 3:
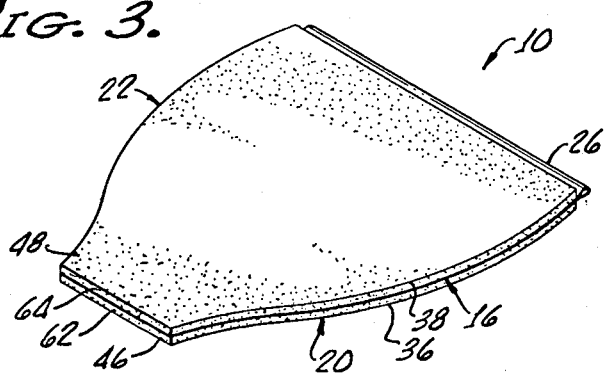
FIG. 3 is a perspective view of an occlusal impression device according to the present invention folded into a position so that the wax impression media is exposed for impression and the occlusion impression device ready for insertion into a mouth to record occlusal impression.

Turning to FIGS. 1, 2 and 3, there is shown an occlusal impression device 10 which generally includes a first impression wax 12 and a second impression wax 14 laminated to a continuous backing, or support, sheet 16. The wax material, or media, 12, 14, may be any suitable soft wax, plastic or similar material, having the proper density and property for being impressed by mandible and maxillary teeth. Often the wax material is formulated so that it can be softened to some extent by contact with hot water before insertion into the mouth of a patient and in this manner provides a means for deforming in response to the pressed engagement therewith by teeth.

The backing sheet 16 is laminated to the waxed media 12, 14, in order to prevent the separation of the wax media 12, 14, from the support sheet 16, as well as preventing separation of pieces (not shown) of the waxed material should fracture occur due to physical abuse and cold temperatures during shipping of the occlusal impression device 10 after use.

As continuous media, the backing sheet 16 includes a first half 20 for supporting the first wax 12 and a second half 22 for supporting a second wax media 14. A central portion 26 functions as a hinge in a manner illustrated in FIGS. 2 and 3 for aligning the first and second wax media 12, 14 with one another, both during insertion into a mouth (see FIG. 4) and for storage purposes, as will be hereinafter described in greater detail. While the present invention may only consist of a single wax media 12 disposed on a back 20 or two separate pieces, such as wax media 12 on the support media 20, and the wax media 14 disposed on the support half 22, it is preferable that the support media 20, 22 are formed from one continuous sheet 16, with the center portion 26 acting as a hinge therebetween. Of course, a separate hinge material may be provided should that be necessary. It should be appreciated that when the device 10 is in a closed position, the wax media 12, 14 are hygienically protected by the sheet 15.

The continuous sheet 16 is preferably formed of a durable paper-like flexible, water-proof material, since the device is to be heated in hot water prior to its use.

In addition, an exposed surface 30 of the concinuous sheet 16 should be suitable for recording indicia, such as by pen or pencil, of the patient's name, date, class of malocclusion, as indicated by lines 32.

As illustrated in the figures, the backing sheet 16, as well as the waxes 12 and 14, are generally flat and coplanar, and each has a mandibular or maxillary arch shape 36, 38 and is sized for engagement with all of the mandible or maxilla teeth 42, 44, see FIG. 4. In addition, a grip portion 46, 48, 44 of the device 10 provides means for inserting the device 10, as shown in FIG. 4 into a mouth 50, without insertion of fingers 52 into the mouth 50.

The arch shape 36, 38 of the waxes 12, 14 being identical provides a means for aligning, or ensuring the alignment of, the waxes with one another. It should be appreciated that other arrangements, such as indents, or marks, (not shown) may be used to align the waxes 12, 14.

The grip portions 46, 48 include an extension of the support means 16 and preferably also the wax 12, 14 which projects from a central portion of the mandibular or maxillary arch with a length l (measured from a continuation of the mandibular or maxillary arch, shown as a dotted line 54, FIG. 1), sufficient to extend beyond the teeth 42, 44 (FIG. 4) when the impression waxes, 12, 14 are inserted into the mouth 50 in a position for engagement with all of the mandible and maxilla teeth 42, 44. It should be appreciated that the length, l, of the grip portions 46, 48 may be sufficient to extend beyond the labia 58.

As shown in the figures, the first and second grip portions 46, 48 may also include an extension 62, 64 of the waxes 12, 14 to provide more rigidity to facilitate the handling of the occlusal device 10 when it is in the exposed position.

FIG. 2 illustrates an intermediate position of the occlusal impression device 10 as it is being unfolded from its storage position shown in FIG. 1 to its exposed position shown in FIG. 3. A gap 70 between the first and second waxes 14, 12 enables the first and second waxes to be folded against one another as shown in FIG. 1, and for the first and second support portions 20, 22 to abut and lay flat against one another as shown in FIG. 3 to facilitate both handling of the open occlusal impression device for insertion and for providing a uniform support for the entire surface 74, 76, when in a folded position, as shown in FIG. 3, in order to enhance the uniformity of the occlusal impression recorded therein.

FIGS. 4, 5 and 6 summarize the procedure and usefulness of the present invention in permanently recording and identifying the occlusal impression of mandible and maxilla teeth. As hereinabove described, the device 10 can be inserted into the mouth 50 of a patient without the insertion of a dentist's fingers, or forceps, thereinto. After the patient has occluded on the device, it is removed with the resultant impressions 80 in the wax 12 shown in FIG. 5. Thereafter, the device is folded to the configuration originally shown in FIG. 1 and now shown in FIG. 6 with the impressions 80 inside the protective support sheet.

In this storage condition, the device 10 may be conveniently shipped and subjected to both abusive handling and cold temperatures without losing the signature bite of the patient, nor the permanently attached indicia recorded on the surface 30 as indicated by the lines 32.

Although there has been described hereinabove a specific arrangement of an occlusal impression device and its method of use, in accordance with the present invention, for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the invention as defined in the appended claims.

What is claimed is:

1. An occlusal impression device comprising:
    first impression means for defoaming in response to pressed engagement therewith;
    second impression means for deforming in response to pressed engagement therewith; and
    first and second support means for supporting said first and second impression means, respectively, said first and second support means being hingeably attached to one another to enable movement of the first and second impression means from a storage position in which the first and second impression means face one another with said first and second support means protecting said first and second impression means from impression, to an exposed position in which the first and second impression means face outwardly from one another ready for simultaneous impression by occlusion of mandible and maxilla teeth.

2. The occlusal impression device according to claim 1 further comprising means for aligning the first and second impression means with one another prior to simultaneous impressions by occlusion of mandible and maxilla teeth.

3. The occlusal impression device according to claim 2 wherein said means for aligning the first and second impression means comprises an identical exterior perimeter on of both the first and second impression means.

4. The occlusal impression device according to claim 1 wherein the first and second support means are formed from a single sheet of flexible material and a central portion of the flexible material function as a hinge.

5. The occlusal impression device according to claim 4 wherein the first impression means is sized for engagement with all of the mandible teeth and the second impression means is sized for engagement with all of the maxilla teeth.

6. The occlusal impression device according to claim 5 wherein the first impression means and first support means are flat, coplanar and have a mandibular arch shape and the second impression means and second support means are flat, coplanar and have a maxillary arch shape.

7. The occlusal impression device according to claim 6 wherein said first support means includes first grip means projecting outwardly from a central portion of the mandibular arch with a length sufficient to extend beyond the labia when the first impression means is inserted into a mouth in position for engagement with all of the mandible teeth, and said second support means includes second grip means projecting outwardly from a central portion of the maxillary arch with a length sufficient to extend beyond the labia when the second impression means is inserted into a position for engagement with all of the maxillary teeth.

8. The occlusal impression device according to claim 7 wherein the first grip means further comprises an extension of the first impression means and the second grip means further comprises an extension of the second impression means.

9. The occlusal impression device according to claim 8 wherein the first and second impression means and the first and second support means are mirror images of one another, respectively.

10. The occlusal impression device according to claim 9 wherein the hinge means is configured for enabling the first and second support means to abut one another when the first and second impression means are in the exposed position.

11. The occlusal impression device according to claim 10 wherein the first and second grip means are aligned with one another when the first and second impression means are in the exposed position and operative for enabling a user to hold the first and second impression means in the open position and simultaneously insert the first and second impression means into the mouth.

12. The occlusal impression device according to claim 11 wherein at least one of the first or second support means has a surface thereon capable of receiving handwritten indicia for recording the use of the occlusal device, said surface being disposed on an opposite side of the first or second support means than a side on which the first or second impression means is disposed, said surface being visible when the first and second impression means are in a storage position.

13. The occlusal impression device according to claim 12 wherein the first and second impression means comprise a wax.

14. An occlusal impression device comprising:
first impression means for deforming in response to pressed engagement therewith;
second impression means for deforming in response to pressed engagement therewith; and
a continuous flexible sheet for aligning said first impression means and said second impression means with one another, said continuous flexible sheet having a first half comprising first support means for supporting said first impression means thereon and a second half comprising second support means for supporting said second impression means thereon, said first and second flexible sheet halves, respectively, including first and second grip means for placing the first and second impression means between mandible and maxilla teeth, said continuous flexible sheet being foldable between said first and second halves thereof to enable movement of the first and second impression means from a storage position in which the first and second impression means face one another with continuous flexible sheet protecting said first and second impression means from impression to an exposed position in which the first and second impression means face outwardly from one another ready for impression, said continuous flexible sheet enabling alignment of the first and second impression means in both the storage and open positions.

15. The occlusal impression device according to claim 14 wherein the impression means and the support means are flat and coplanar and each has a mandibular or maxillary arch shape.

16. The occlusal impression device according to claim 15 wherein the first and second impression means are sized for engagement with all of the mandible and maxilla teeth, respectively.

17. The occlusal impression device according to claim 16 wherein said first and second grip means comprise an extension of said first and second support means, respectively, and project outwardly from a central position of the mandibular or maxillary arch with a length sufficient to extend beyond the labia when the impression means is inserted into a mouth in position for engagement with all of the mandible or maxilla teeth.

18. The occlusal impression device according to claim 17 wherein said first grip means further comprises an extension of the first impression means and said second grip means further comprises an extension of the second impression means.

19. The occlusal impression device according to claim 18 wherein the first and second impression means are mirror images of one another, respectively.

20. The occlusal impression device according to claim 19 wherein the first and second grip means are aligned with one another and abut one another when the first and second impression means are in the exposed position and are operative for enabling a user to hold the first and second impression means in the open position and simultaneously insert the first and second impression means into the mouth.

21. The occlusal impression device according to claim 20 wherein said continuous flexible sheet has a surface thereon capable of receiving handwritten indicia for recording the use of the occlusal appliance, said surface being disposed on an opposite side of the said continuous flexible sheet than a side on which the first and second impression means are disposed, said surface being visible when the first and second impression means are in a storage position.

22. The occlusal impression device according to claim 21 wherein the first and second impression means comprise a wax.

* * * * *